(12) United States Patent
Kief

(10) Patent No.: US 6,303,152 B1
(45) Date of Patent: Oct. 16, 2001

(54) PROCESS FOR THE PRODUCTION OF SUBSTANCES THAT HAVE BEEN BACTERICIDALLY TREATED AND/OR EXHIBIT IMMUNE-MODULATORY ACTIVITY, AND THE USE THEREOF

(76) Inventor: Horst Kief, Londoner Ring 105, D-6700 Ludwigshafen (DE)

( * ) Notice: Subject to any disclaimer, the term of this patent is extended or adjusted under 35 U.S.C. 154(b) by 0 days.

(21) Appl. No.: 08/031,346

(22) Filed: Mar. 15, 1993

Related U.S. Application Data

(63) Continuation of application No. 07/935,194, filed on Aug. 26, 1992, now abandoned, which is a continuation-in-part of application No. 07/550,572, filed on Jul. 10, 1990, now abandoned, which is a continuation-in-part of application No. 07/115,251, filed on Oct. 30, 1987, now abandoned.

(30) Foreign Application Priority Data

Oct. 30, 1986 (EP) .................................................. 86115097

(51) Int. Cl.⁷ .......................... A61K 35/00; A61K 35/14; A61K 35/22

(52) U.S. Cl. .......................... 424/529; 424/530; 424/531; 424/532; 424/533; 424/534; 424/545

(58) Field of Search ...................................... 424/529, 530, 424/531, 532, 533, 534, 545; 604/4

(56) References Cited

U.S. PATENT DOCUMENTS 4,632,980 * 12/1986 Zee et al. .............................. 530/380
4,684,521 * 8/1987 Edelson ................................. 424/529
4,748,120 * 5/1988 Wiesehahn ......................... 435/173.3

FOREIGN PATENT DOCUMENTS

3109691 * 9/1982 (DE) .

* cited by examiner

*Primary Examiner*—Jean C. Witz
(74) *Attorney, Agent, or Firm*—Levy & Grandinetti

(57) ABSTRACT

A process is disclosed for the production of immune-genetically active suspensions of which the initial substances are fluids or tissues from the human or animal body. Autohemotherapy, immune-stimulatory and/or immune-suppressive effects are employed. The suspensions thus produced can be used as pooled sera as desired.

26 Claims, 3 Drawing Sheets

Schematic of an immune - regulative treatment
with Autohemologous Immune Therapy (AHIT)

PROCESS FOR THE PRODUCTION OF SUBSTANCES THAT HAVE BEEN BACTERICIDALLY TREATED AND/OR EXHIBIT IMMUNE-MODULATORY ACTIVITY, AND THE USE THEREOF

CROSS-REFERENCE TO RELATED APPLICATIONS

This is a continuation of application Ser. No. 07/935,194, filed Aug. 26, 1992, now abandoned, which in turn is a continuation-in-part of application Ser. No. 07/550,572, filed Jul. 10, 1990, now abandoned, which in turn is a continuation-in-part of application Ser. No. 07/115,251, filed Oct. 30, 1987, now abandoned. The entire disclosure of this latter application, including the drawings thereof, is hereby incorporated in this application as if fully set forth herein.

BACKGROUND OF THE INVENTION

1. Field of the Invention

The invention relates to a process for the production of germicidally treated and/or immune-modulatory active substances and to the use of the substance produced by this process, referred to for brevity as a "suspension", in particular to influence the immune system in the human and animal organism.

2. Brief Description of the Background of the Invention Including Prior Art

In the present state of medical science and technology, there are various ways of influencing the immune system of the body.

An example is by passive or active vaccination, i.e. by the stimulation of antibodies or by the direct application of antibodies, whereby either suppressive or stimulatory processes can be produced (definitions of medical terms in particular according to "Pschyrembel" clinical dictionary, Walter de Gruyter, Berlin-New York, 1977).

Desensitization has achieved particular importance in which the triggering antigen is first introduced to the organism at a very high dilution and then in increasing doses, so as to neutralize the excessive antibody reactions. Disadvantages of this process are the low success rate, the very prolonged treatment time, and the relatively limited spectrum of indication of allergic illnesses.

A simple yet successful process is the injection of autologous blood. One such process is known in which dilutions of autologous blood are treated with suspensions of aluminum hydroxide, analogous to the binding of vaccines on aluminum hydroxide in processes known to date, whereby the binding of the protein on the oxide certainly produces not only a certain depot effect for the erythrocyte material and the plasma proteins, but also a partial isolation of immune-relevant proteins.

This process has not achieved any great acceptance since it does not work reliably in the broad spectrum of indications.

Another method that should also be mentioned is an alternative method in which the patient's blood is very strongly oxidized by an ozone-oxygen mixture and then returned to the organism. Individual observations indicate that here immune-modulatory processes are triggered, too.

The use of suspensions for oxidation therapy is also described in particular in German Patent Specification 31 09 691, which refers to the autohemotherapy of Wolff, and more particularly, to the hyperbaric ozone therapy using venous blood of Kief, for which a device for extracorporeal bacteriocidal treatment is elaborated upon. The oxidation process of Wehrlie is also described.

In the proposals of Wolff and Kief, blood from the patient's body, and this alone, is used as the initial substance and subjected to an oxidation treatment and then reinfused as such. This is thus done in an exclusive manner, and there is only one oxidation step.

SUMMARY OF THE INVENTION

1. Purposes of the Invention

It is an object of the invention to provide a process for influencing the immune system of mammals.

It is another object of the invention to provide a method for creating suppressive and stimulative effects in a mammal.

It is a further object of the invention to provide a method of producing an oxidized blood.

These and other objects and advantages of the present invention will become evident from the description which follows.

2. Brief Description of the Invention

The invention is based on the observation that oxidized autologous blood can, in some cases, exhibit suppressive effects while in other similar cases it can show a stimulatory effect. Elucidation of this contradictory observation led to the discovery that oxidized or ozonized plasma often has an immune-suppressive effect, while a similarly treated erythrocyte concentrate just as often has an immune-stimulatory effect. Further clarification of exact occurrence led to the discovery that even deproteinized serum can still trigger immune-modulatory processes.

Urine which in this respect can be regarded in a somewhat simplified manner as an electrolyte solution that has been filtered from the blood through the kidneys and selectively concentrated can, when administered by injection, also trigger immune processes.

While the use of urine as a "desensitizing agent" was formerly often practiced in naturopathic medicine, it has since been forgotten due to the fact that the disinfecting additives usually employed in the past, namely thymol and phenol, are themselves somewhat toxic and are unsuitable for use as additives. However, urine cannot be used unfiltered and unsterilized because of the risk of injection abscesses.

Based on these discoveries it is disclosed, according to the invention, to fractionate the initial substance which, besides human or animal blood, can also be a tissue or an initial substance multiplied by culturing, or even urine.

The novel features which are considered as characteristic for the invention are set forth in the appended claims.

The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1:
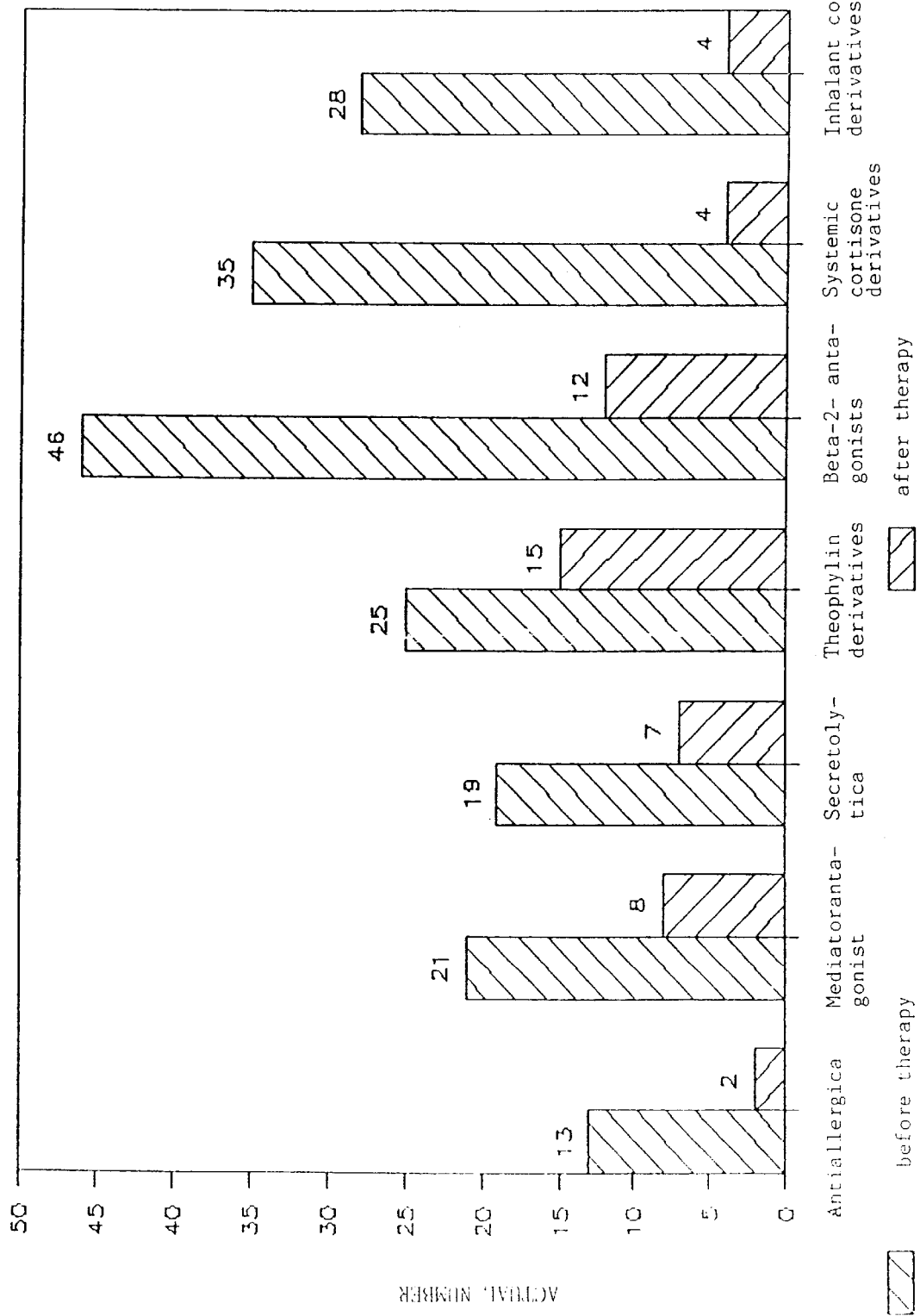
FIG. 1 is a graph illustrating a decrease of medication use in a study of 65 asthmatic patients after autohemologous immune therapy (AHIT)—actual number.

In accordance with the invention, there is provided a process for the production of germicidally treated and/or immune-modulatory active substances (suspensions) by an extracorporeal route, whereby the initial substances taken from an ill individual are subjected to an oxidant by means of ozone, oxygen and/or UV radiation, where in the initial substances are fractionated. Tissue can be the initial substance. The initial substance can be multiplied through culturing. The initial substance can be urine. The initial substance can be comminuted to sub-cell size (cell lysis).

A cell lysis can be performed mechanically, enzymatically and/or osmotically. Each of the fractions can be separately filtered and again, or only then, be subjected to the oxidation. The addition of carbonyl group carriers can occur in the application process. The addition can take place before the last oxidation. The carbonyl group carrier is of aromatic structure. The carbonyl group carrier can be of aliphatic structure.

Repeated oxidation can characterize the invention process. The ozone content of the $O_2$–$O_3$ mixture can be regulated. The ozone concentration of the $O_2$–$O_3$ mixture can be from about 40 to 80 ng $O_3$ per ml $O_2$. Ascorbic acid can also be added. The ascorbic acid can be added before the last oxidation step.

The initial substance or its fractions can be diluted after the oxidation. The dilution can be carried out with ozonized water. The treated fractions can be recombined to a uniform dilution. The final suspension can be shock-frozen. The final suspension can be freeze-dried. Halogens, preferably chlorine or iodine, can be added to the suspension.

The suspensions can be used as pooled sera (for other individuals).

The suspensions produced can be used as a potable dilution. The suspensions produced can be used as an inhalable solution. The suspensions produced can be used for rubbing in.

In detail, the initial substances employed can be fluids or tissues obtained from the human or animal body; based on autohemotherapy, immune-stimulatory and/or immune-suppressive effects. Original substances of the human organism include general blood, urine, and solid tissue. Blood is fractionated into a) cellular components and b) humoral components. The suspensions thus produced can (also) be used as pooled sera.

The initial substance, for example the blood of a sick individual, is aspirated into a sterile plasma bottle in known way as commonly performed and is heparinized to prevent coagulation. The amount of heparin added depends of course on the amount of blood aspirated. The cellular components of the original substances are subdivided, for example by high-speed centrifuge, into plasma and thrombocytes, lymphocytes, granulocytes, and erythrocytes. The lymphocytes are separated by autocytophoresis into its subpopulation. The protein substances of the plasma are separated from each other in an electric field. In the case of solid tissue, one proceeds either from the outset to mechanically homogenize the tissue in order to subject it thereafter to a further proteolytic splitting by way of tissue-own proteases, trypsin, and papainases, or the cells are separated from each other by elastase. Thereafter, in case of malignant tissue, the malignant tissue is deprived of its immunogenic protective layer by neuraminidase.

Residual air is then sucked out of the bottle or container with the fractionated material. The thus resulting fractions, which are wholly intact cells in the case of the last-described process and which are subcellular particles or components in the process described farther above, are subsequently subjected during several steps and phases to an ozonization process.

An ozone-oxygen mixture is blown in under pressure in a conventional way, for example, as described in the above-mentioned patent specification. As mentioned above, tissue and/or urine can be used as the initial substance instead of blood. The latter likewise meets all the requirements for an non-toxic, well-tolerated and, above all, effective immune modulant.

Contrary to the state of the art where the ozonization process occurs with untreated blood, in the method according to the invention, the ozonization occurs with the fractionated blood, that is with blood where the individual fractions are exposed to the uninhibited attack of the ozone, and thus provokes a substantially stronger alteration process of the proteins, the lipids, and other structures. However, the stronger the molecular changes and modifications of these structures, the stronger is also the immune-modulatory effect exerted by these substances. This appears to be a generally acknowledged law, which is now employed in a useful manner.

The fractionation is necessary, and in fact in the cellular area up to the so-called cell organellae. In this respect, the hemolysate of the invention was electron-microscopically investigated. Small bodies of sub-cell size were found which, even after an extreme ozonization, still exhibited organellae character. According to the opinion of persons skilled in the art, the small bodies seem to be so-called peroxysomes, which exhibit an increased resistance relative to $O_2$ radicals. The presence of peroxysomes also explains the discrepancy relative to the sub-cell size.

The instant invention discloses a fractionation method of cells to individual cell organellae in connection with an ozonization or, respectively, in connection of ozonolysates. The fractionated parts are subsequently joined together by recombination to an immune-modulatory substance in the presence of oxidizing agents such as ozone.

In case of a concentration of 50 micrograms per milliliter of molecular oxygen, the ozonization occurs, for example, for a duration of one minute. In this case, the total masses amount to more than 10,000 micrograms of ozone. The multiple ozonization in the case of blood occurs, for example, in that initially whole blood is ozonized, followed by the captured partial fractionation of leucocytes or erythrocytes, for example, and subsequently, after cold-shock treatment, again the homogenization.

The cause of the surprising effect of the invention may be based on the following considerations.

1. The cellular constituents of the human and animal blood, namely white and red blood cells and thrombocytes, are embedded in the protein of the plasma, which in turn is dissolved in serum, the entire mixture thus forms an equilibrated and buffered system that protects and maintains itself according to the principles of regulation and counter-regulation. If the blood is now fractionated, the mutually regulating protective mechanisms of the individual systems break down and the selected fraction, as for example washed erythrocytes, is directly exposed, devoid of its protective coating, to a noxin, such that a controlled partial isolation of the proteins of cellular constituents of the blood can exert a considerably stronger immune-modulatory effect.

2. The addition of ozone or other (strong) oxidations for immune-modulatory isolation of blood or blood fractions may be regarded as a process that is very close to what occurs in nature, since the body itself often relies on oxidative processes as part of its natural defense for example, the white blood cells in defense against infection in the context of the "respiratory burst" by means of oxygen radicals which is to be understood as those parts of the body's own defense that occurs by means of oxidation.

3. Most germs, bacteria or viruses, produce an organotropic effect, i.e. in relation to our organ "blood", they only occupy particular constituents thereof. For example, the AIDS virus has a particular lymphocyte subpopulation, so that only after fractionation of the blood does the virucidal, fungicidal and bacteriocidal effect of the oxidant lead to an optimal and specific destruction of antigens and thus to specific immune stimulation.

4. The cells can defend themselves from the strong oxidizing attack by means of particular enzyme systems in the cell membrane. Only after breaking up and/or destruction of this structure are very many important immune-modulatory substances accessible to oxidation. This break-up and destruction of protective structures can occur through mechanical influences (homogenization), non-physiological temperatures (freezing), osmosis or proteolytic enzymes, e.g. pepsin, papain or bromelain. The resulting "fracture sites" of particular protein fractions, new potential points of attack for ozone or other oxidants, emphasize the importance of repeated oxidation of blood or of selected blood fractions. What has been described above in connection with "blood" also applies, within the scope of the invention and expressed in a simplified manner, to the other initial substances mentioned.

During oxidation it is of only subsidiary importance whether the oxidant is supplied to the medium concerned as a finished product from a Siemens discharge tube or, for example, generated in the material being treated itself by saturation with oxygen and possibly repeated irradiation with UV light.

If we consider the organotrophy of different: antigens and the associated antibodies in various systems, the next step of a specific immune stimulation, with a possible similar specific selective immune suppression in another organ system, becomes clear.

After separate treatment with ozone of the fractions according to the invention, either part or all of the fractionated initial substances are then recombined into a uniform suspension. It can be appropriate prior to ozonization to multiply the individual fractions by culturing them, as for example a lymphocyte population as the carrier of particular antibodies. By means of a selective oxidation, an increased "blood fraction" is attained of a concentrated antibody suspension which isolates in a "physiological manner" through the oxidant and, on renewed contact with the organism, triggers a specific anti-autoantibody process that compensates the original pathological immunization process. The renewed contact with the donor organism can be brought about parenterally, e.g. by injection, or orally, i.e. by drops, or even by inhalation or simple skin contact, e.g. by rubbing into the skin.

Using blood as an example, by subsequent recombination of selected and separately oxidized (especially by ozonization) fractions or hemolysates of the white and red systems of blood cells, of plasma, of defibrinated serum and/or urine to a uniform dilution, a medication is obtained that has not only specific immune-stimulatory properties of an active vaccine but also, so far as is therapeutically indicated, an immune-suppressive, organ-related effect similar to that of a passive vaccine. Hemolysate is understood, in the sense of the invention, as a suspension of plasma and intracellular fluid of the of variable composition.

A practical procedure is to centrifuge the erythrocytes from autologous blood treated with an oxidant as described above, remove the plasma and treat it again with an oxidant. Thereafter, the erythrocytes are treated again (after repeated washings) with an oxidant and partially suspended in distilled water such that an osmosis-induced burst occurs. Once again they are treated with an oxidant. In special cases a urine filtrate, treated with an oxidant, is added either to the serum or to the erythrocyte suspension. Ideally, the desired hemolysate can be controlled by varying the oxygen-ozone concentration. It has been found that, in the ideal case, the concentration of the ozone-oxygen mixture in the oxidant is between 40 and 80 ng $O_3$ per ml $O_2$.

After recombination of the mentioned fractions, with the possible addition of the urine filtrate, an extremely potent immune modulant is obtained that has, depending on its quantitative composition, immune-stimulatory and immune-suppressive properties. Proceeding in the manner described, as for example with the blood serum of a particular group of patients, e.g. polyarthritics, a pooled serum can be obtained that can be used with success against rheumatism.

During addition of the oxidant by the supplementing carbonyl group carriers of aromatic or aliphatic structure, their sharply oxidizing potential can be shifted into a physiological state, similar to the quinones in the respiratory process. It is therefore disclosed, as a further aspect of the invention and depending on the desired intensity of the oxidation process, to add, e.g. ascorbic acid (vitamin C), at a particular point in the oxidant procedure. This specific additive may be regarded as an ideal carbonyl group carrier of aromatic structure because of its conversion into dehydroascorbic acid during the chemical metabolism. The conversion of vitamin C into dehydroascorbic acid can be terminated at any desired point in the process by freezing, in particular by shock-freezing. Carbonyl group carriers of aliphatic structure can also be used.

In certain cases, the immune-stimulatory effect of the recombined suspension can be so potent that it should only be used in diluted forms, e.g. 1:10, particularly in the initial phase of the treatment. It is especially advantageous to perform this dilution with ozonized water for injection. Injectable water is not only totally sterile but also beneficial for extended shelf-life of the diluted suspension.

In a further development of the invention the addition of halogens, for example chlorine or bromine, to the suspensions described is of particular importance to the body's natural defenses, e.g. by stimulation of a Haber-Weiss reaction and the resulting prolongation of in vitro oxidative processes in vivo. In the known Haber-Weiss reaction, a substance, e.g. iodine, is oxidized into an unstable compound which supplies oxygen as a radical: the substance is again oxidized and the process starts from the beginning. This chain reaction continues until the oxygen present is fully metabolized. The added halogens can be in the form of acids and/or salts as well as in complex forms.

The present invention description discloses the effect of such a hemolysate, produced by ozonolysis from a blood fraction, to endogenic but also to exogenic (in case of foreign individuals) blood-cell cultures on the respective person and the required initial substances. A particular advantage of the invention process is the absolute absence of side effects, which is usually not the case upon the use of medication. The absence of side effects is particularly important in case of endogenic applications.

Following are some detailed examples relating to a recombination of the fractionated blood components and to their use.

1. Relation Initial Substance/Ozone Gas and Ozonization Process

The amount of gas volume applied per volume of liquid depends on the liquid volume and always amounts to at least twice the volume of liquid employed.

If 300 ml gas are required for ozonizing 150 ml blood at 50 micrograms, then the total mass $O_3$ can be calculated and is always indicated, in this case 15,000 micrograms. In order to completely decompose blood by ozonolysis, i.e. to bring the erythrocytes to dissolution, 12,000 micrograms per 5 ml of blood are required. In order to subject 5 ml of blood to an ozonolysis, accordingly, there are required 200 ml of an $O_2/O_3$ mixture at an $O_3$ concentration of 60 micrograms per milliliter of oxygen. However, this holds only in relation to the corpuscular components. If one works exclusively with sera, about half the volume of gas relative to the volume of liquid of the solution will be sufficient.

An indication of the content of the ozone after the procedure is not possible since the ozone is used up completely and does not have a residue.

2. Splitting of Blood Molecules with Ozone

The immune-globulins of the sera can be split longitudinally with ozone, i.e. a two-part fractionation. Moreover, the variable segment can be separated by means of trypsin from the constant segment of an immune-globulin. Thus, one obtains thereby a six-split of the immune-globulin by combination of both methods ozone and enzyme. These six-split immune-globulins have a marked stimulation effect on the suppressor cells in vivo. In the case of sera, splitting is performed, i.e. a fractionation is performed up into the molecular region and, in the case of cellular blood components, up into the organellae region.

3. Recombination of Washed Erythrocytes with Leucocytes

Leucocytes are fractionated to a cell-organellae size. A recombination of washed erythrocytes with such leucocytes has a stimulation effect on the white blood composition with a particular stimulation of the natural killer cells and macrophages. This process can be contrasted to ozonolytic splitting. If the immune-globulins are treated with ozone according to the above process, they have an excellent immune-modulatory effect, in particular also on diseases of the respiratory system, for example asthma, spastic brochitis, and, in fact, exclusively on this organ group.

4. Combination of Ozonized Urine Filtrates with Sera

Ozone-treated urine filtrates are combined with a sera, which sera were treated with ozone as described above. An excellent medication is obtained to treat immune-genetically caused diseases of the respiratory path system, be they of an allergic or of an intrinsic nature (cf. also Decrease of Drug Use).

5. Ascorbic Acid Addition to Hemolysates

The corpuscular components erythrocytes and leucocytes, are separated and 1 gram of ascorbic acid is added before the last ozonization step to the hemolysate of the cell concentrate after dissolution. This allows to use the hemolysate as immune stimulant. In this case, the amount of the cell concentrate is at least 50 ml, up to a maximum of 80 ml.

6. Dilution of Hemolysates

The hemolysate obtained under ascorbic acid addition is extremely potent. The effect can be clinically observed and determined in a dilution of $1:10^{12}$. In case of treatment of autoimmune diseases, it is standard to dilute with a dilution of $1:10^9$, since the effects of these lysates in the sense of a desensibilisation, i.e. a first deterioration of the symptomatic, are often too strong. Thus, the level of the dilution is to be determined individually. It can however be said in general that in most cases a dilution of $1:10^{12}$ represents an upper limit.

7. Decrease of Drug Use Requirements a Patient in Case Obstructive Lung Diseases In the following Table 1, it is shown that autohemologous immune therapy (AHIT) brings about a drastic reduction in the use of pertinent antiasthmatically effective medications. During the course of a treatment series, respectively after conclusion of a treatment series, during which period 65 patients have undergone autohemologous immune therapy, there occurred partially a drastic lowering in the need of medication.

Figure 2:
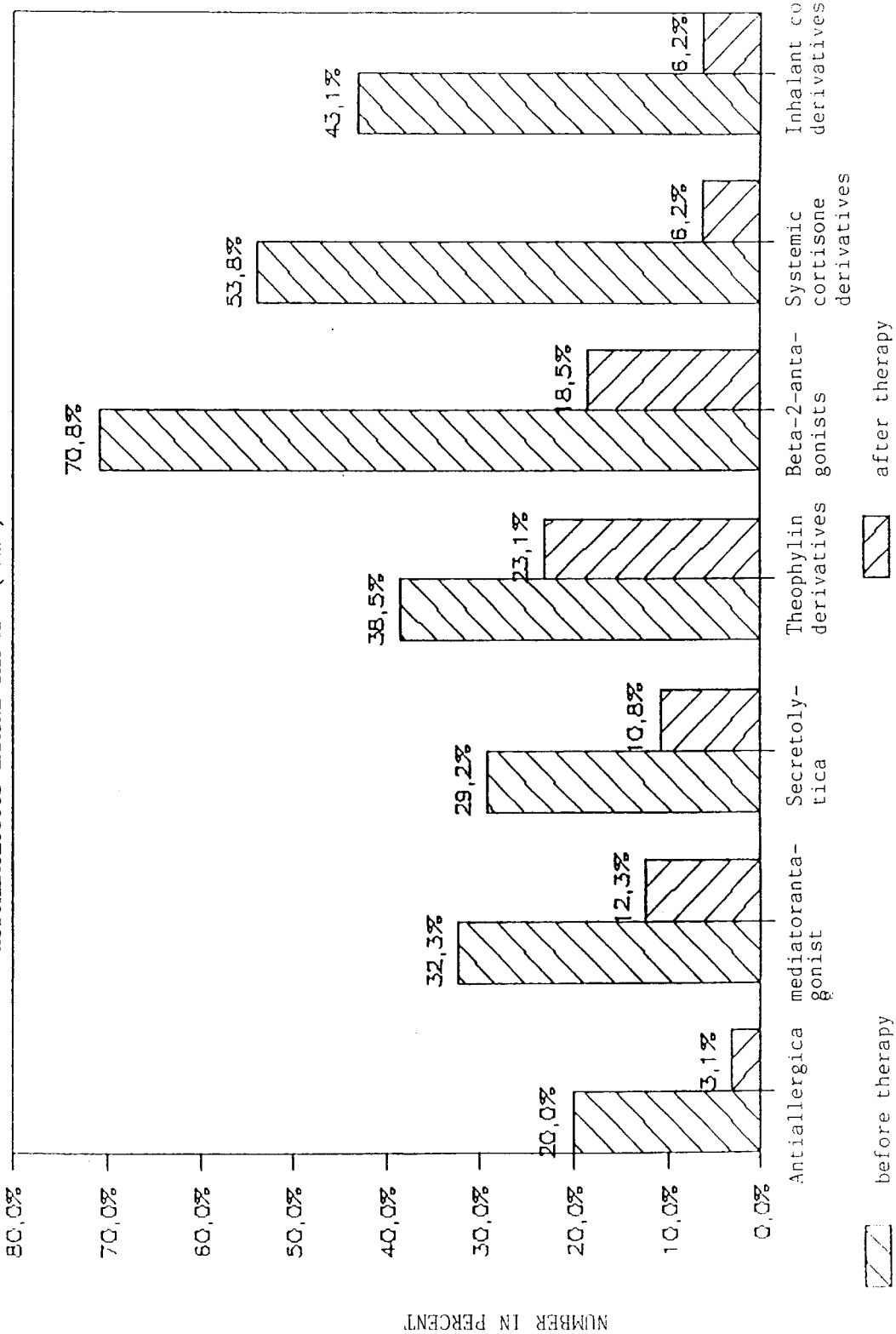
FIG. 2. is a graph similar to the graph of FIG. 1, however illustrating the number in percent.

These tests in relation to autohemologous immune therapy (AHIT) have resulted in the statistical tables, as illustrated in FIGS. 1 and 2, relating to a treatment of patients, in particular asthmatic patients, in order to obtain a lowering of medication use.

TABLE 1

| Medication | before treatment | | after treatment | |
| --- | --- | --- | --- | --- |
| | Number of Patients | % | Number of Patients | % |
| Antiallergica | 13 | 20.0 | 2 | 3.1 |
| Mediatorantagonists | 21 | 32.3 | 8 | 12.3 |
| Secretolytica | 19 | 29.2 | 7 | 10.8 |
| Theopbyllin derivatives | 25 | 38.5 | 15 | 23.1 |
| Beta-2-antagonists | 46 | 70.8 | 12 | 18.5 |
| Systemic cortisone derivatives | 35 | 53.8 | 4 | 6.2 |
| Inhalant cortisone derivatives | 28 | 43.1 | 4 | 6.2 | t - test −5.00572 6th degree of freedom
($p < 0.01$)

Of particular importance in the test results as shown in FIGS. 1 and 2 is a decrease in the need of systemic corticoids of nearly 90%, as compared to the exclusive oral use of this group of medication, and in case of inhalative cortisone derivatives by more than 85%.

These results are important since obstructive lung diseases, in particular bronchial asthma, are increasing dramatically worldwide. The number of research programs being financed today by the federal government for this particular section of the health system is a measure for the urgency, with which new treatments are researched in order to counter the increase of immune-induced diseases of the skin and the respiratory system. A solution for this situation is offered by the autohemologous immune therapy (AHIT) of this example.

Diagram A illustrates a short-term study of patients with asthma treated with autohemologous immune treatment (AHIT).

8. The Treatment of Neurodermitis with Autohemologous Immune Therapy (AHIT)

The invention discloses the application of autologous blood derivatives gained by proteolysis and ozonolysis of selected autologous blood fractions as an effective therapeutical method for treating the acquired immune deficiency. Exact follow-ups of the lymphocytic subpopulation in the above-mentioned patients revealed that the number of helper cells and suppressor cells may be controlled by these remedies and suggested that the application of these protein/cell mixtures might also show good results in case of autoimmune diseases. The efficiency of the therapy is demonstrated by way of example of neurodermatitis and supported by statistical data.

Figure 3:
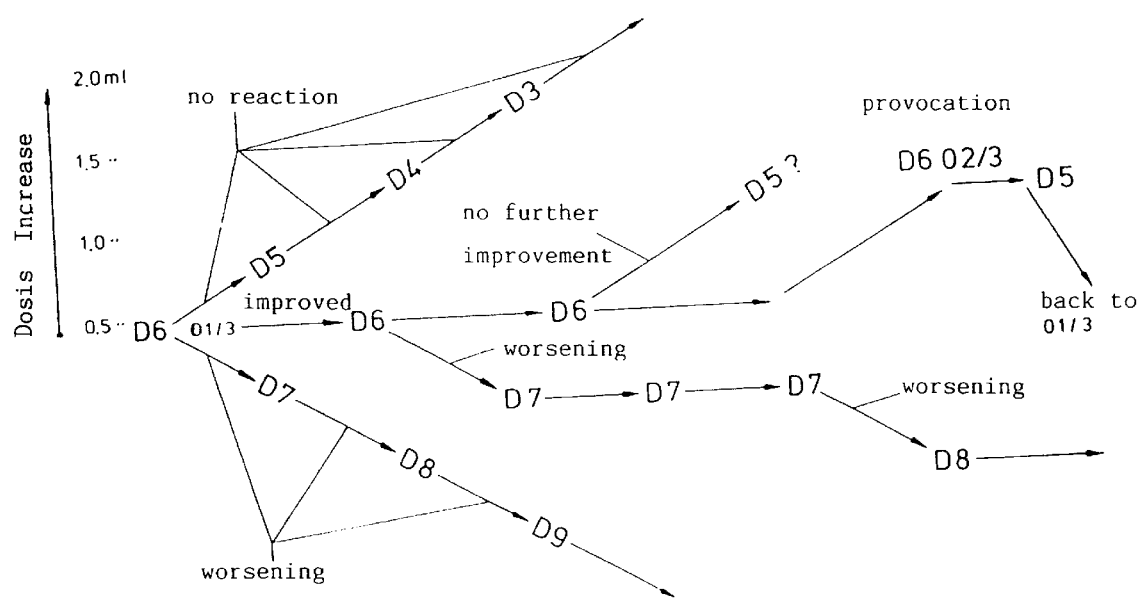
FIG. 3 is a schematic diagram of an immune-regulative treatment with autohemologous immune therapy (AHIT).

An overview of the immune regulative treatment of a patient is illustrated in FIG. 3.

The invention method allows therapy of neurodermatitis, which had been a very thankless subject for both the orthodox medicine and the naturopathy.

Diagram B illustrates a long-term study over a 2½-year period of patients with neurodermatitis treated with autohemologous immune treatment (AHIT). Diagram C illustrates a representative cross-section (April-August) of said study.

The surprising result of the studies carried out includes a full remission and a relaps in 40% of 10 patients who were not treated in this manner, as well as a full remission without relaps in 37% of the patients of this study over a period of 2½ years. The autologous blood derivatives gained by the method which is briefly described are very potent remedies and thus have to be carefully measured. The correct dosage is described in detail.

List of diseases (indicated by numerals) and of proposed agents (indicated by letters) used for treatment of these diseases.

1. Allergy, atopic Dermatitis
   a. Hemolysate 01/3 (patient-own immune globulins, albumine, and thrombocytes subjected to additional catalytic reduction of oxygen-radical processes) in dilution $D_0$, $D_1$–$D_6$ (dilution of 1:1 to $1:10^6$);
   b. Hemolysate 02/3 (washed erythrocytes, granulocytes, and lymphocytes subjected to additional catalytic reduction of oxygen-radical processes) in dilution $D_0$, $D_1$–$D_6$ (dilution of 1:1 to $1:10^6$);
   c. Drops (coded yellow and green) including Hemolysate 01/3 (described above) and Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$) for adults and in dilution $D_0$–$D_4$ (dilution of 1:1 to $1:10^4$) for children;

2. Colitis ulcerosa, Morbus Crohn, Psoriasis
   a. Hemolysate 01/2 (patient-own immune globulins, albumine, and thrombocytes additionally enriched with a hemolysate with light-chain immune globulins consisting of urine filtrate) in dilution $D_0$, $D_1$–$D_6$ (dilution of 1:1 to $1:10^6$);
   b. Hemolysate 02/2 (washed erythrocytes, granulocytes, and lymphocytes additionally enriched with a hemolysate with light-chain immune globulins consisting of urine filtrate) in dilution $D_0$, $D_1$–$D_6$ (dilution of 1:1 to $1:10^6$);
   c. Drops (coded yellow and green) including Hemolysate 01/3 (described above) and Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$) for adults and in dilution $D_0$–$D_4$ (dilution of 1:1 to $1:10^4$) for children;

3. Parkinson
   a. Hemolysate 01/1 (patient-own immune globulins, albumine, and thrombocytes additionally excited with the redox press by admixture of an ascorbic acid/DHAS-mixture during processing procedure)
   b. Hemolysate 02/1 (washed erythrocytes, granulocytes, and lymphocytes additionally excited with the redox press by admixture of an ascorbic acid/DHAS-mixture during processing procedure);

4. Hepatitis, multiple sclerosis
   a. Hemolysate 02/1 (washed erythrocytes, granulocytes, and lymphocytes additionally excited with the redox press by admixture of an ascorbic acid/DHAS-mixture during processing procedure) in dilution $D_0$–$D_2$ (dilution of 1:1 to $1:10^2$);
   b. Drops (coded yellow and green) including Hemolysate 02/1 (described above) in dilution $D_0$–$D_2$ (dilution of 1:1 to $1:10^2$);
   c. UF (coded green) including Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$)

5. Chronic Hepatitis
   a. Hemolysate 01/1 (patient-own immune globulins, albumine, and thrombocytes additionally excited with the redox press by admixture of an ascorbic acid/DHAS-mixture during processing procedure) in dilution $D_0$–$D_2$ (dilution of 1:1 to $1:10^2$);
   b. Hemolysate 02/1 (washed erythrocytes, granulocytes, and lymphocytes additionally excited with the redox press by admixture of an ascorbic acid/DHAS-mixture during processing procedure) in dilution $D_0$–$D_2$ (dilution of 1:1 to $1:10^2$);
   c. Drops (coded yellow and green) including Hemolysate 02/1 (described above) in dilution $D_0$–$D_2$ (dilution of 1:1 to $1:10^2$) and in dilution $D_0$–$D_4$ (dilution of 1:1 to $1:10^4$) for children;
   d. UF (coded green) including Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$)

6. Chronic Sinusitis, bronchial asthma, nasal allergy
   a. Hemolysate 01/2 (patient-own immune globulins, albumine, and thrombocytes additionally enriched with a hemolysate with light-chain immune globulins consisting of urine filtrate) in dilution $D_0$, $D_1$–$D_6$ (dilution of 1:1 to $1:10^6$);
   b. Hemolysate 02/2 (washed erythrocytes, granulocytes, and lymphocytes additionally enriched with a hemolysate with light-chain immune globulins consisting of urine filtrate) in dilution $D_0$–$D_6$ (dilution of 1:1 to $1:10^6$);
   c. Drops of Hemolysate 01/3 (coded yellow and described above) and drops of Hemolysate 03 (sterile urine filtrate, subjected to a process of longitudinal and cross-sectional splitting of immune globulins carried out in several steps and phases and oxidization of the split immune globulins; coded green) in dilution $D_0$–$D_2$ (dilution of 1:1 to $1:10^2$) for adults and in dilution $D_0$–$D_4$ (dilution of 1:1 to $1:10^4$) for children;
   d. Nose spray (coded white) contained Hemolysate 05 (inhalant of the identical components);
   e. Inhalant (coded blue) contained Hemolysate 04 (nasal drops, where the Immune components of the nasal drops consist of Hemolysate 01 (patient-own immune globulins, albumine, and thrombocytes) and of Hemolysate 03 (sterile urine filtrate, subjected to a process of longitudinal and cross-sectional splitting of immune globulins carried out in several steps and phases and oxidization of the split immune globulins);

7. Rheumatic type indications, scleroderma Sjögren syndrome a. Hemolysate 01/4 (patient-own immune globulins, albumine, and thrombocytes excited in oxygen-radical processes by admixture of iodine-potassium iodide) in dilution $D_0$, $D_1$–$D_6$ (dilution of 1:1 to $1:10^6$);

b. Hemolysate 02/4 (washed erythrocytes, granulocytes, and lymphocytes excited in oxygen-radical processes by admixture of iodine-potassium iodide) in dilution $D_0$, $D_1$–$D_6$ (dilution of 1:1 to $1:10^6$);

c. Drops (coded yellow and green) including Hemolysate 01/4 (patient-own immune globulins, albumine, and thrombocytes excited in oxygen-radical processes by admixture of iodine-potassium iodide) and Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$) for adults and in dilution $D_0$–$D_4$ (dilution of 1:1 to $1:10^4$) for children;

8. All carcinomas a. Hemolysate 02/1 (washed erythrocytes, granulocytes, and lymphocytes additionally excited with the redox press by admixture of an ascorbic acid/DHAS-mixture during processing procedure) in dilution only $D_0$ (dilution of 1:1) and Hemolysate 08/1 (autolysate consisting of leukemia tissue additionally excited with the redox press by admixture of an ascorbic acid/DHAS-mixture during processing procedure) in dilution $D_0$, $D_1$–$D_4$ (dilution of 1:1 to $1:10^4$);

b. Drops (coded yellow and green) including Hemolysate 02/1 (described above) in dilution only $D_0$ (dilution of 1:1);

c. UF (coded green) including Hemolysate 03 (sterile urine filtrate, subjected to a process of longitudinal and cross-sectional splitting of immune globulins carried out in several steps and phases and oxidization of the split immune globulins) in dilution $D_0$–$D_2$ (dilution of 1:1 to $1:10^2$)

TABLE 3

DESIGNATIONS OF THE HEMOLYSATES

All hemolysates are designated by a number code, which informs the user and the patient about the content. The number before the slash (/) designates the components and the number following the slash (/) designates the processing method. The initial materials for the various hemolysates are as follows:

| | |
|---|---|
| Hemolysate 01 | patient-own immune globulins, albumine, and thrombocytes |
| Hemolysate 02 | washed erythrocytes, granulocytes, and lymphocytes |
| Hemolysate 03 | sterile urine filtrate, subjected to processing method /0 |
| Hemolysate 04 | nasal drops, where the immune components of the nasal drops consist of 01 and 03 |
| Hemolysate 05 | inhalant of the identical components |
| Hemolysate 06 | erythrocyte cytoplasm, which was subjected to the processing method /0 |

TABLE 3-continued

DESIGNATIONS OF THE HEMOLYSATES

All hemolysates are designated by a number code, which informs the user and the patient about the content. The number before the slash (/) designates the components and the number following the slash (/) designates the processing method. The initial materials for the various hemolysates are as follows:

| | |
|---|---|
| Autolysate 07 | autolysate consisting of patient-own cancerous tissue |
| Autolysate 08 | autolysate consisting of leukemia tissue. |

Processing Methods
/0 longitudinal and cross-sectional splitting of immune globulins carried out in several steps and phases and oxidization of the split immune globulins
/01 additional excitation of the redox press by admixture of an ascorbic acid/DHAS-mixture during processing procedure
/02 additional enrichment of the hemolysate with light-chain immune globulins consisting of urine filtrate
/03 additional catalytic reduction of oxygen-radical processes
/04 Excitement of oxygen-radical processes by admixture of iodine-potassium iodide Below is described a standard treatment plan in case of neurodermatitis by a long period (16 weeks) treatment.

In case of neurodermatitis a patient is treated 2–3 times weekly with Hemolysate 01/3 (patient-own immune globulins, albumine, and thrombocytes subjected to additional catalytic reduction of oxygen-radical processes) or with Hemolysate 02/3 (washed erythrocytes, granulocytes, and lymphocytes subjected to additional catalytic reduction of oxygen-radical processes) according to period of treatment.

In the first week the patient is treated with 0,5–1 ml of Hemolysate 01/3 in dilution $D_6$ (dilution of $1:10^6$). Upon observation of a negative reaction or of (initial) worsening of symptoms the patient is treated only with oral medication (described below). Later in time a treatment with Hemolysate 01/3 is renewed.

In the second week and in the third week the patient is treated with 1,0–2,0 ml of Hemolysate 01/3 in dilution $D_6$ (dilution of $1:10^6$). At a patient exhibition a negative reaction is treated with 0,5 of Hemolysate 01/3 in dilution $D_6$ (dilution of $1:10^6$).

In the 4th week the patient is treated with 0,5–1 ml of Hemolysate 01/3 in dilution $D_5$ (dilution of $1:10^5$).

In the 5th week the patient is treated with 1,0–2 ml of Hemolysate 01/3 in dilution $D_5$ (dilution of $1:10^5$).

In the 6th week the patient is treated with 0,5–1 ml of Hemolysate 01/3 in dilution $D_4$ (dilution of $1:10^4$). At negative reaction patient is treated with 1,0 of Hemolysate 01/3 in dilution $D_5$ (dilution of $1:10^5$).

In the 7th week the patient is treated with 1,0–2 ml of Hemolysate 01/3 in dilution $D_4$ (dilution of $1:10^4$). At negative reaction patient is treated with 0,5 of Hemolysate 01/3 in dilution $D_4$ (dilution of $1:10^4$).

In the 8th week the patient is treated with 0,5–1 ml of Hemolysate 02/3 in dilution $D_6$ (dilution of $1:10^6$). Upon observing a negative reaction the patient is treated with 1,0–2 ml of Hemolysate 01/3 in dilution $D_4$ (dilution of $1:10^4$).

In the 9th week the patient is treated with 1,0–2 ml of Hemolysate 01/3 in dilution $D_4$ (dilution of $1:10^4$).

In the 10-th week the patient is treated with 1,0 ml of Hemolysate 02/3 in dilution $D_5$ (dilution of $1:10^5$). Upon a negative reaction the patient is treated with of Hemolysate 01/3 in dilution $D_4$ (dilution of $1:10^4$).

In the 11th week the patient is treated with 1,0 ml of Hemolysate 01/3 in dilution $D_4$ (dilution of $1:10^4$).

In the 12th week the patient is treated with 1,0 ml of Hemolysate 01/3 in dilution $D_3$ (dilution of $1:10^3$).

In the 13th and 14-th week the patient is treated with 1,0 ml of Hemolysate 02/3.

In the 15th week the patient is treated with 1,0 ml of Hemolysate 01/3.

In the 16th week the patient is treated with 1,0 ml of Hemolysate 01/3 in dilution $D_0$ (dilution of 1:1).

The patient is treated additionally with drops of Hemolysate 01/3 (patient-own immune globulins, albumine, and thrombocytes subjected to additional catalytic reduction of oxygen-radical processes), coded yellow, in dilution $D_2$ (dilution $1:10^2$) representing an oral side medication. After two weeks, the patient is treated additional with drops of Hemolysate 03 (sterile urine filtrate, subjected to a process of longitudinal and cross-sectional splitting of immune globulins carried out in several steps and phases and oxidization of the split immune globulins), coded green, in dilution $D_2$ (dilution $1:10^2$), then drops of Hemolysate 03 in dilution $D_1$ (dilution 1:10), then drops of Hemolysate 03 as "prime tincture". Adults start with 10 drops on an empty stomach in the morning, increase the dosis by one drop daily to 15 drops, up to a maximum of 20 drops. Children start with 5 drops on an empty stomach in the morning, increase the dosis up to 10 drops. Lower starting doses or dilutions of a higher ordinal number ($D_3$ to $D_6$; dilution of $1:10^3$ to $1:10^6$) can become necessary for infants and patients, suffering from neurodermatitis since childhood. The drops are to be taken daily in the morning with a glass of water.

In FIG. 3 there is shown a schematic diagram of an immune—regulative treatment with Autohemologous Immune Therapy (AHIT). A treatment of a patient is started with 0,5 ml of Hemolysate 01/3 (patient-own immune globulins, albumine, and thrombocytes subjected to additional catalytic reduction of oxygen-radical processes) in dilution $D_6$ (dilution of $1:10^6$). The treatment of the patient is initially tried with Hemolysate 01/3 having a decreased dilution $D_5$ to $D_3$ (dilution of $1:10^5$ to $1:10^3$) and having an increased dosis 0,5 to 2,0 ml (top—left side of schema) and with increased dilution $D_7$ to $D_9$ (dilution of $1:10^7$ to $1:10^9$) and decreased dosis. The patient is treated back with 0,5 ml of Hemolysate 01/3 in dilution $D_6$ (dilution of $1:10^6$). When observing no reaction or when observing worsening, then a treatment with Hemolysate 01/3 of increased dilution $D_7$ (dilution of $1:10^7$) (middle—bottom part of schema) or decreased dilution $D_5$ (dilution of $1:10^5$) (middle—top part of schema) is renewed. The patient is treated back with 0,5 ml of Hemolysate 01/3 in dilution $D_6$ (dilution of $1:10^6$). In case no further improvement reaction or worsening of the situation occurs, then the patient is treated with Hemolysate 02/3 (washed erythrocytes, granulocytes, and lymphocytes subjected to additional catalytic reduction of oxygen-radical processes) in dilution $D_6$ to $D_5$ (dilution of $1:10^6$ to $1:10^5$) as provocation to observe how the patient reacts. Then the patient is treated again with Hemolysate 01/3.

Asthma
Representative Cross-section (April-August)

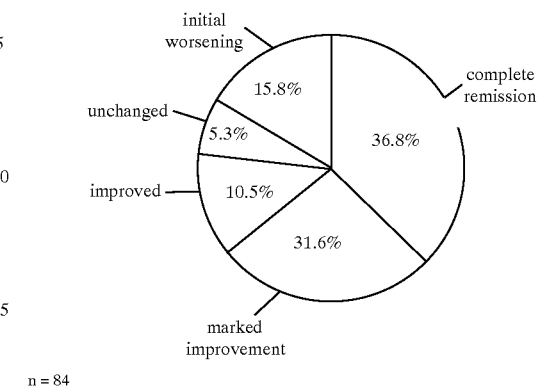

n = 84

Treatment of Neurodermitis with Autohemologous

Immune Therapy (AHIT)

Long-Term Study over a 2 ½-year period

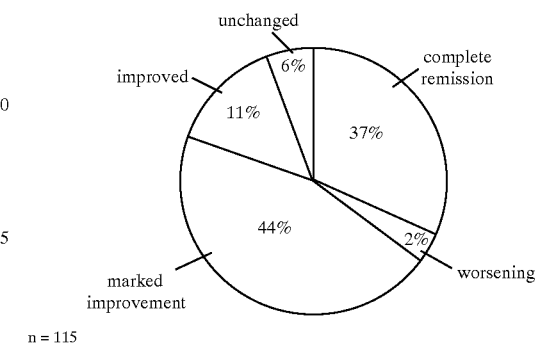

n = 115

Diagram B

Neurodermitis
Representative Cross-section (April-August)

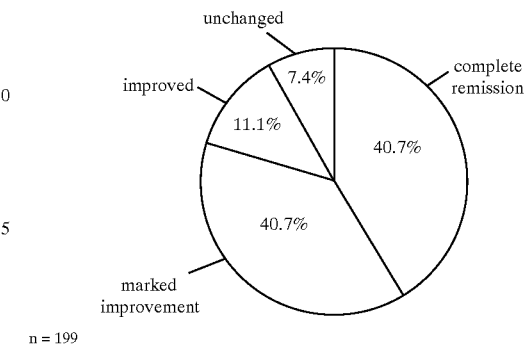

n = 199

Diagram C
9. Ozonizing Erythrocyte Plasma

Erythrocytes are brought to a bursting by means of a cold shock. This erythrocyte pulp is subsequently centrifuged and the excess, i.e. the pure erythrocyte plasma, is captured therefrom and ozonized. An excellent erythropoetic stimulant is produced for the human bone marrow as well as an excellent, and relatively fast acting roborant product, without thereby generating a large amount of methemoglobin.

10. Ozonizing Urine-Derived Fractions

Due to the filtering effect of the kidneys, light-chain immune globulins as well as other proteins are contained in the urine. The light-chain immune globulins can be separated from each other in an electrical field. In this case, based on the specific composition of the urine, the ratio of the light-chain immune globulins to the remaining idiotypes of the immune globulin can be varied with respect to each other upon admixing of plasma.

As a rule, urine has to be regarded as an infected medium since xenogerms or extrinsic germs in the urine are continuously expelled from the outer genital areas. Consequently, the urine has to be filtrated, preferably with 22 micrometers single-use, discardable filters, in order to assure a complete absence of bacteria.

It will be understood that each of the elements described above, or two or more together, may also find a useful application in other types of processes differing from the type described above.

While the invention has been illustrated and described as embodied in the context of a process for the production of substances that have been bacteriocidally treated and/or exhibit immune-modulatory activity, and the use thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A process for the production of germicidally treated suspensions comprising
   taking body fluids from a person suffering from a member of the group of illnesses consisting of atopic neurodermatitis, bronchial asthma and nasal allergies, colitis ulcerosa, Parkinson, Morbus Crohn, Hepatitis, chronic Hepatitis, chronic Sinusitis, Psoriasis, rheumatic-type indications, carcinomas, multiple sclerosis, and scleroderma Sjögren syndrome and combinations thereof;
   desaggregating the body fluids by reducing the body fluids to sub-cell size substances by cell lysis;
   subjecting a member selected of the group consisting of body fluids, sub-cell size substances, and mixtures thereof to an oxidant by exposing the member selected of the group consisting of body fluids, sub-cell size substances to a member selected from the group consisting of ozone, oxygen, UV radiation, and mixtures thereof for obtaining suspensions exhibiting immune-modulatory active properties.

2. The process for the production of germicidally treated suspensions according to claim 1 further comprising
   treating the body fluids on an extracorporeal route.

3. The process for the production of germicidally treated suspensions according to claim 1 wherein the body fluids are a member selected from the group consisting of tissue, urine, and mixtures thereof.

4. The process for the production of germicidally treated suspensions according to claim 1, wherein the body fluids include cells, further comprising
   multiplying the cells of the body fluids by means of culturing prior to a desaggregating step.

5. The process for the production of germicidally treated suspensions according to claim 1 further comprising
   recombining ozone-treated desagaregated substances of sub-cell size to a uniform dilution and forming a finished substance.

6. The process for the production of germicidally treated suspensions according to claim 1 wherein the cell lysis is performed mechanically, enzymatically and osmotically.

7. The process for the production of germicidally treated suspensions according to claim 1 further comprising
   separately filtering each of the desagregated, sub-cell substances;
   subjecting a member selected from the group consisting of urine, tissue, and mixtures thereof, to an oxidant, and subjecting again the separately filtered sub-cell size substances and mixtures thereof to an oxidant.

8. The process for the production of germicidally treated suspensions according to claim 1 further comprising
   admixing carbonyl group carriers of aromatic structure to one of the body fluids and the sub-cell size substances and forming a mixture.

9. The process for the production of germicidally treated suspensions according to claim 1 further comprising admixing carbonyl group carriers of aliphatic structure to the sub-cell size substances; and subjecting the mixture to an oxidant.

10. The process for the production of germicidally treated suspensions according to claim 1 wherein the body fluid is a serum;
    desaggregating the serum by mechanical means to form desaggregated immune globulins;
    dividing the desaggregated immune globulins by contacting with ozone for generating a variable size segment and a constant size segment;
    separating the variable size segment with trypsin from the constant segment for obtaining a hexa-division of the immune-globulin;
    contacting in vivo fluids comprising suppressor cells with the hexa-division of the immune globulin.

11. The process for the production of germicidally treated suspensions according to claim 1 wherein the desaggregated body fluids are leucocytes desaggregated to sub-cell size parts and washed erythrocytes; and further comprising
    ozonizing the washed erythrocytes;
    ozonizing the sub-cell size parts derived from leucocytes;
    recombining the ozonized erythrocytes with the ozonized sub-cell size leucocytes to a recombined oxidized mixture;
    adding the recombined oxidized mixture to human blood for stimulating natural killer cells and macrophages.

12. The process for the production of germicidally treated suspensions according to claim 1 further comprising
    repeatedly oxidizing the body fluids and sub-cell size substances; and
    controlling the ozone content of an oxygen $O_2$–ozone $O_3$ mixture.

13. The process for the production of germicidally treated suspensions according to claim 1 further comprising employing an ozone gas as an oxidant having an ozone concentration in an oxygen $O_2$–ozone $O_3$ mixture of from 40 to 80 ng ozone $O_3$ per ml oxygen $O_2$.

14. The process for the production of germicidally treated suspensions according to claim 1 further comprising admixing ascorbic acid to the body fluids or to the sub-cell size substances and forming a mixture.

15. The process for the production of germicidally treated suspensions according to claim 14 further comprising admixing the ascorbic acid to the sub-cell size substances and forming a mixture; and subjecting the mixture to an oxidant.

16. The process for the production of germicidally treated suspensions according to claim 1, wherein the oxidant is ozonized water, further comprising diluting the body fluids of desaggregated, sub-cell size substance with an aqueous solution.

17. The process for the production of germicidally treated suspensions according to claim 1 further comprising recombining the treated desaggregated substances to a uniform medium.

18. The process for the production of germicidally treated suspensions according to claim 1 further comprising chill quenching the sub-cell size substances.

19. The process for the production of germicidally treated suspensions according to claim 17 further comprising freeze-drying the sub-cell size substance.

20. The process for the production of germicidally treated suspensions according to claim 1 further comprising admixing halogens to the sub-cell size substances.

21. The process for the production of germicidally treated suspensions according to claim 1 further comprising chill quenching erythrocytes causing the erythrocytes to burst apart and to form an erythrocyte pulp;

centrifuging the erythrocyte pulp for separating an erythrocyte plasma;

ozonizing the erythrocyte plasma;

contacting human bone marrow with the ozonized erythrocyte plasma for obtaining an erythropoetic stimulation.

22. The process for the production of germicidally treated suspensions according to claim 5 further comprising filtering urine with single-use discardable filters for assuring complete absence of bacteria;

separating light-chain immune globulins derived from urine from each other under the effect of an electric field by electrophoresis;

varying the ratio of light chain immune globulin to the remaining idiotypes of the immune globulin;

admixing plasma to the light-chain immune globulin;

recombining the treated desaggregated substances to a uniform dilution and forming a finished substance.

23. The process for the production of germicidally treated suspensions according to claim 1 further comprising separately filtering each of the desaggregated, sub-cell substances prior to subjecting the respective sub-cell size substances thereof to an oxidant.

24. The process for the production of germicidally treated suspensions according to claim 1 further comprising desaggregating said body fluids by reducing the body fluids to sub-cell size substances by cell lysis thereby generating a first fraction and a second fraction;

subjecting the first fraction of sub-cell size substances to an oxidant with a member selected from the group consisting of ozone, oxygen, UV radiation and mixtures thereof;

subjecting the second fraction of sub-cell size substances to an oxidant with a member selected from the group consisting of ozone, oxygen, UV radiation and mixtures thereof;

combining the first fraction and the second fraction.

25. A process for the production of germicidally treated suspensions comprising taking body fluids formed of tissue from a person suffering from a member of the group of illnesses consisting of atopic neurodermatitis, bronchial asthma and nasal allergies, allergies, colitis ulcerosa, Parkinson, Morbus Crohn, Hepatitis, chronic Hepatitis, chronic Sinusitis, Psoriasis, rheumatic-type indications, carcinomas, multiple sclerosis, and scleroderma Sjögren syndrome and combinations thereof;

fractionating the tissue by reducing the tissue to sub-cell size substances by cell lysis for obtaining a first fraction and a second fraction;

subjecting the first fraction to an oxidant with a member selected from the group consisting of ozone, oxygen, UV radiation and mixtures thereof;

subjecting a member selected from the group consisting of the second fraction, a separately generated fractionated sub-cell size substance, tissue, and mixtures thereof to an oxidant with a member selected from the group consisting of ozone, oxygen, UV radiation and mixtures thereof;

recombining the treated first fraction and the treated second fraction.

26. A process for the production of germicidally treated suspensions comprising withdrawing blood from a person suffering from a member of the group of illnesses consisting of atopic neurodermatitis, bronchial asthma and nasal allergies, allergies, colitis ulcerosa, Parkinson, Morbus Crohn, Hepatitis, chronic Hepatitis, chronic Sinusitis, Psoriasis, rheumatic-type indications, carcinomas, multiple sclerosis, and scleroderma Sjögren syndrome and combinations thereof;

treating said blood with an oxidant;

centrifuging the erythrocytes out of said blood thereby removing plasma from the centrifuged erythrocytes;

treating the plasma with an oxidant;

treating the centrifuged erythrocytes with an oxidant;

partially suspending the oxidized erythrocytes in distilled water so as to burst these erythrocytes through osmosis;

treating a urine filtrate with oxidant;

adding the oxidized urine filtrate to the oxidized plasma;

combining the fraction containing the erythrocytes and the fraction containing the plasma and the urine filtrate for generating a combined suspension;

contacting an immune system with the combined suspension for modulating the immune-active properties of the immune system.

\* \* \* \* \*